(12) United States Patent
Haigh

(10) Patent No.: US 7,528,367 B2
(45) Date of Patent: May 5, 2009

(54) ION MOBILITY SPECTROMETER

(75) Inventor: Paul E. Haigh, Londonderry, NH (US)

(73) Assignee: GE Homeland Protection, Inc., Newark, CA (US)

( * ) Notice: Subject to any disclaimer, the term of this patent is extended or adjusted under 35 U.S.C. 154(b) by 5 days.

(21) Appl. No.: 11/875,536

(22) Filed: Oct. 19, 2007

(65) Prior Publication Data
US 2008/0093549 A1    Apr. 24, 2008

Related U.S. Application Data

(63) Continuation of application No. 11/328,968, filed on Jan. 9, 2006, now abandoned.

(51) Int. Cl.
   *H01J 49/40* (2006.01)
   *H01J 49/00* (2006.01)
   *G01N 30/70* (2006.01)
(52) U.S. Cl. .................... 250/287; 250/281; 250/282; 250/286; 250/288
(58) Field of Classification Search ............ 250/281, 250/282, 283, 286, 287, 288
See application file for complete search history.

(56) References Cited

U.S. PATENT DOCUMENTS

| | | | |
|---|---|---|---|
| 3,522,425 A | 8/1970 | Rich | |
| 5,200,614 A * | 4/1993 | Jenkins | 250/286 |
| 5,338,931 A * | 8/1994 | Spangler et al. | 250/287 |
| 5,396,065 A | 3/1995 | Myerholtz et al. | |
| 5,491,337 A * | 2/1996 | Jenkins et al. | 250/287 |
| 6,509,562 B1 * | 1/2003 | Yang et al. | 250/287 |
| 6,690,005 B2 * | 2/2004 | Jenkins et al. | 250/287 |
| 6,765,198 B2 * | 7/2004 | Jenkins et al. | 250/287 |
| 2007/0158548 A1 * | 7/2007 | Haigh | 250/287 |
| 2008/0093549 A1 * | 4/2008 | Haigh | 250/288 |

FOREIGN PATENT DOCUMENTS

| | | |
|---|---|---|
| EP | 0 528 426 A | 2/1993 |
| WO | WO 93/19481 A | 9/1993 |
| WO | WO 2005/059539 A | 6/2005 |

* cited by examiner

*Primary Examiner*—Bernard E Souw
(74) *Attorney, Agent, or Firm*—Global Patent Operation

(57) ABSTRACT

An ITMS includes an inlet for receiving a sample that will be tested for a substance of interest. The inlet communicates with an ionization chamber and a drift chamber communicates with the downstream end of the ionization chamber. A first grid electrode extends across the downstream end of the ionization chamber and a second grid electrode is slightly downstream from and parallel to the first grid electrode. A slight potential bias is applied to the first grid electrode to hold the ions in the potential well between the first and second grid electrodes. However a pulse is applied periodically to the first grid electrode to accelerate ions into the drift chamber. The accumulation of the ions in the potential well prior to generation of the pulse results in a thinner band of ions ejected into the drift chamber and hence achieves higher resolution.

10 Claims, 1 Drawing Sheet

ION MOBILITY SPECTROMETER

CROSS REFERENCE TO RELATED APPLICATIONS

This application is a continuation of U.S. patent application Ser. No. 11/328,968 filed on Jan. 9, 2006 entitled "Ion trap Mobility Spectrometer", which is incorporated by reference herein in its entirety.

BACKGROUND OF THE INVENTION

1. Field of the Invention

The invention relates to a detector to test for trace amounts of substances of interest.

2. Description of the Related Art

Terrorism risks continue at transportation facilities, government buildings, banks, restaurants, hotels and other locations where there is a significant flow of pedestrian or vehicular traffic. As a result, virtually all airports and many other buildings now include apparatus for detecting trace amounts of explosives.

Narcotics are illegal and insidious. Furthermore, it is known that many terrorist organizations fund their terrorism through the lucrative sale of narcotics. Accordingly, many airports and other public buildings recognize the need to check for narcotics.

Ion mobility spectrometers have been commercially available since about 1970, and are used to test for the presence of at least selected constituents in a stream of sample gas. An ion mobility spectrometer can be used to detect the presence of explosives in the sample gas. The typical prior art ion mobility spectrometer includes an ionization region and a drift region. A sample of air to be analyzed is fed into the ionization region on a stream of carrier gas containing a halogenated compound. The carrier gas is ionized by $\beta$ particles emitted from radioactive walls of the ionization chamber to form positive ions and electrons. The electrons are captured by gases, causing a series of reactions that lead to the ionization of the halogen. Molecules of interest form ions by interaction with these gas phase ions. An electric field is established in the ionization region. The polarity of the field can be set to direct the ions of interest towards the drift region of the prior art detector. The ions travel through the drift region and towards a collector electrode at the end of the drift region opposite the ionization region. The drift time to the collector electrode varies in accordance with the size-to-change ratio of the ions. A current will be established at the collector electrode at different times depending upon the arrival times of the ions. This current is amplified and converted to a voltage for signal analysis purposes. Specific substances of interest will have a unique drift time. The detector can be calibrated to identify substances of interest based on that drift time and produce an alarm signal to the operator. Unfortunately, the conventional ion mobility spectrometer allows ions to pass into the drift region for only a short period of time. Ions arriving at the entry to the drift region at all other times are discharged. As a result, most ions are discharged in older ion mobility spectrometers and the ionization and collection efficiency of older ion mobility spectrometers is less than 0.01%. Accordingly, older ion mobility spectrometers can not detect many substances of interest that might be present in a sample.

U.S. Pat. Nos. 5,200,614 and 5,491,337 each disclose an ion mobility spectrometer (ITMS) that provide enhanced ability to detect trace amounts of substances of interest. The ion mobility spectrometer shown in U.S. Pat. No. 5,200,614, carries a sample vapor into a detector inlet on a carrier gas. The carrier gas may be doped with a low concentration vapor employed as a charge transfer mediator. Sample molecules of interest are fed through an inlet and a diffuser, and into an ionization chamber. The prior art ionization chamber has a cup-shaped metal wall and a radioactive material is disposed in the chamber. An open grid electrode is at the downstream end of the ionization chamber and normally is at the same potential as the metal walls of the ionization chamber. Thus, a largely field-free space is defined in the ionization chamber. Electrons and ion charges build up this field-free space and interact with the sample molecules under bombardment by beta-particles from the radioactive walls. However, a field is established periodically across the ionization region to sweep the ions into a drift region of the ITMS. The ions in the drift region experience a constant electric field maintained by annular electrodes, and are impelled along the drift region towards a collector electrode for analysis on the basis of their spectra. The field across the grid electrode and metal cup of the ionization chamber is reduced again to zero after about 0.2 mS and the ion population again is allowed to build up in the chamber preparatory to the imposition of the next field. The polarity of the fields of the prior art detector are chosen on the basis of whether the detector is operated in a negative or positive ion mode. A negative ion mode usually is preferred when detecting explosives. U.S. Pat. No. 5,491,337 discloses an ion mobility spectrometer with enhanced performance in a positive mode to test for the presence of trace amounts of narcotics. U.S. Pat. No. 6,765,198 discloses an ion mobility spectrometer that can analyze a single sample in a negative mode to test for explosives and in a positive mode to test for narcotics. The disclosures of U.S. Pat. Nos. 5,200,614, 5,491,337 and 6,765,198 are incorporated herein by reference.

Detectors that incorporate the teaching of U.S. Pat. Nos. 5,200,614, 5,491,337 and 6,765,198 are marketed by GE Security, Inc. and have proved to be very effective and commercially successful. However, a demand still exists for detectors with improved resolution. In this regard, it has been determined that the resolution of the peaks detected by the above-described detectors are dependent on the width of the pulse of ions introduced into the drift chamber as well as the broadening that the clouds of ions experience in the drift chamber due to diffusion, electronic repulsion and other factors. It also has been determined that the area of the outer periphery of the ionization chamber close to the grid electrode create a higher electric field during the introduction of ions into the drift chamber. Ions in these areas of higher electric fields would be introduced into the drift region before ions in lower electric field areas of the ionization chamber inwardly from the peripheral walls that define the ionization chamber. This difference in ion introduction time widens the pulse of ions and degrades the overall peak resolution of the detector. Accordingly, an object of the invention is to provide a detector with improved resolution.

SUMMARY OF THE INVENTION

The invention relates to a detector and preferably a detector that includes an ion mobility spectrometer. The detector has an inlet for receiving a sample that will be tested for substances of interest. The sample may be received by: a flow of air traveling past a human being or package; particles transferred from a package or luggage to a sample; particles transferred from a suspect's hand to a ticket or card; particles transferred directly from the hand of the suspect to a sample collection surface of the detector; or other optional ways for receiving samples that may have substances of interest. The detector includes a heater for heating the collected sample sufficiently to vaporize the sample. The detector then includes a supply of a transporting gas for transporting the vaporized sample into the detector. The apparatus for collecting the sample, vaporizing the sample and transporting the sample into the detector can be a known apparatus, such as those disclosed in U.S. Pat. Nos. 5,200,614, 5,491,331, 6,073,499, U.S. Patent Publication No. 2005/0019220 or pending U.S. patent application Ser. No. 10/929,915, the disclosures of which are incorporated herein by reference.

The detector has an inlet for receiving the gas stream that includes the vaporized sample that will be tested for the presence of at least one substance of interest. The detector further includes an ionization chamber that communicates with the inlet and a drift chamber that communicates with the ionization chamber.

The ionization chamber preferably is a generally cup-shaped structure with an inlet and an outlet. The inlet to the ionization chamber receives the gas that includes the vaporized sample that will be tested for the presence of at least one substance of interest. The outlet end of the ionization chamber preferably is cross-sectionally larger than the inlet. The ionization chamber preferably is formed from a metallic material and includes or consists of a radioactive material. A preferred ionization chamber is formed from a gold plated metal cup and a radioactive foil is applied to an inner peripheral surface of the cup. A preferred radioactive material is nickel$^{63}$.

The drift chamber has an inlet end that communicates with the outlet of the ionization chamber. The drift chamber also includes an outlet end, and a collection electrode is disposed near the outlet end of the drift chamber. Drift electrodes are disposed between the inlet end of the drift chamber and the collector electrode and function to maintain field conditions conducive to a controlled downstream drift of ions from the ionization chamber to the collector electrode.

The detector of the subject invention further includes a first grid electrode at the outlet from the ionization chamber and a second grid electrode downstream from the first grid electrode. A slight potential bias is applied to the first grid electrode with respect to the walls of the ionization chamber and with respect to the second grid electrode during the ion-accumulation stage of the operation of the detector. As a result, ions created in the ionization chamber are attracted to the first grid electrode. More specifically, a negative bias is applied for positive ion mode operation (e.g., narcotics detection) and a positive bias is applied for negative ion mode operation (e.g., explosive detection). The potential difference between the first grid electrode and the ionization chamber and the second grid electrode is small, but effectively creates a "potential well". Ions accumulate in the potential well between the first and second grid electrodes during the ion accumulation stage of the operation.

The detector introduces ions into the drift chamber by creating an electric field between the first and second grid electrodes for a short duration. This distinguishes from the prior art detector where the ions are introduced into the draft chamber by creating an electric field between the cup-shaped walls of the ionization chamber and the grid electrode. The first and second grid electrodes of the subject invention are coplanar, substantially parallel and close together. As a result, the electric field generated between the first and second grid electrodes is substantially uniform. Ions of a given type accelerated in this potential well between the first and second grid electrodes move substantially simultaneously and at substantially the same speed towards the drift region. As a result, a thinner band of ions is introduced into the drift chamber, thereby improving resolution. Additionally, sensitivity is improved because the ions are concentrated in the relatively small space defined by the potential well between the first and second grid electrodes.

DETAILED DESCRIPTION OF THE PREFERRED EMBODIMENT

Figure 1:
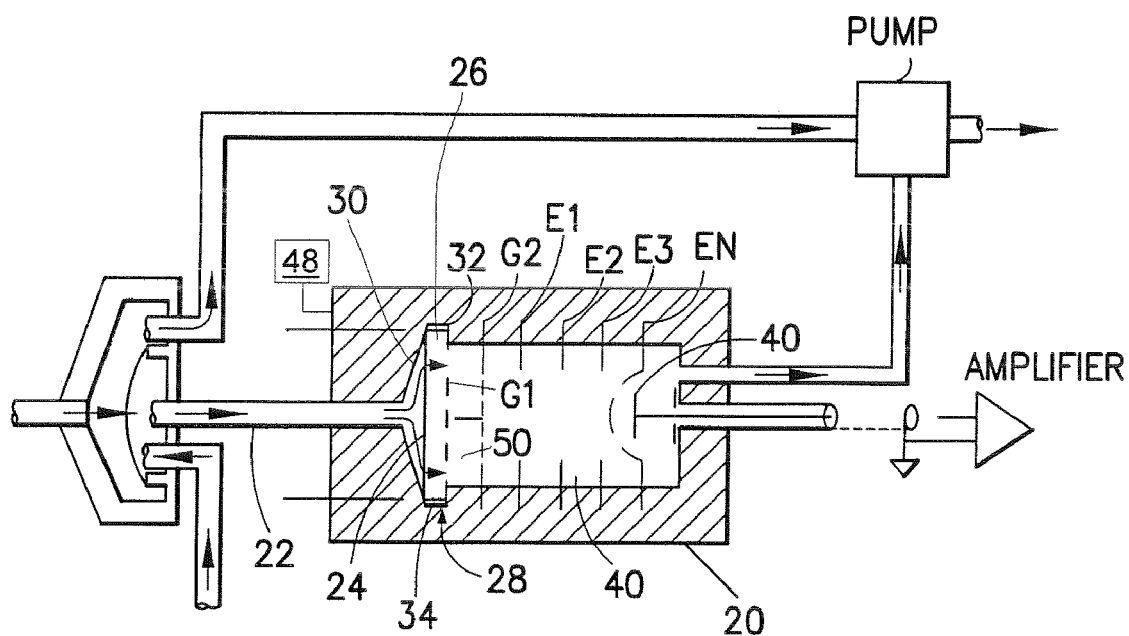
FIG. 1 is a schematic cross-sectional view of an ion mobility spectrometer detector in accordance with the subject invention.

An ion mobility spectrometer in accordance with the subject invention is illustrated in FIG. 1. The ion mobility spectrometer includes a generally cylindrical detector 20 having an inlet 22 at one end for receiving a sample air of interest borne by a carrier gas. The carrier gas may be doped with a low concentration vapor employed as a charged transfer mediator, as described in the above-referenced patents that have been incorporated herein by reference. The sample air, carrier gas and any dopant molecules that may be employed pass through the inlet 22 and are spread by a diffuser 24 into an ionization chamber 26. The ionization chamber 26 includes a cup 28 formed from a gold-plated conductive metal with an inlet end wall 30 that extends outwardly from the inlet 22 and a cylindrical or flared sidewall 32 that extends downstream from the inlet end wall 30. A foil 34 is applied to the inner surface of the cylindrical sidewall 32. The foil 34 is formed from a radioactive material such as nickel$^{63}$ or tritium that emits β particles. A first grid electrode G1 extends across the downstream end of the cylindrical sidewall 32. A second grid electrode G2 is disposed slightly downstream from the first grid electrode G1 and is aligned substantially parallel thereto.

A drift chamber 40 communicates with the downstream end of the ionization chamber 26. The drift chamber 40 includes a plurality of open grid electrodes $E^1$-$E^N$ aligned substantially parallel to one another and downstream from the second grid electrode G2. The collector electrode 42 is substantially at the downstream end of the drift chamber 40 and communicates with a processor and readout device. The downstream end of the drift chamber 40 also includes an exhaust outlet for permitting an outflow of gas from the ion mobility spectrometer 20.

A slight potential bias is applied by a controller 48 to the first grid electrode G1 with respect to both the cup 28 and the second grid electrode G2 during the ion accumulation phase of an operation cycle of the ion mobility spectrometer. In this regard, a negative bias is applied to the first grid electrode G1 during the positive ion mode operation for detecting narcotics and a positive bias is applied to the first grid electrode G1 during the negative ion mode operation for detecting explosives. As a result, ions created in the ionization chamber 26 are attracted to the first grid electrode G1 during the ion accumulation phase of the operation of the ion mobility spectrometer 20. This lower potential of the first grid electrode G1 between the cup 28 and the second grid electrode G2 creates a potential well 50, and ions tend to accumulate in the area of the potential well 50.

The ion mobility spectrometer then is subjected to a kick-out phase for introducing the ions into the drift chamber 40. More particularly, a short duration (e.g., 0.1-0.2 mS) pulse is applied to the first grid electrode G1 while adjusting the second grid electrode G2 to approximately the highest potential in the drift field of the drift chamber 40, which typically is about 1,000 volts. Thus, ions are introduced into the drift chamber 40 by the creation of the electric field between first and second grid electrodes G1 and G2 instead of by creating an electric field merely between the cup 28 and the first grid electrode G1, as in the prior art. The first and second grid electrodes G1 and G2 are planar, parallel and closely spaced. This differs from the non-planar configuration of the cup 28. As a result, the electric field generated between the first and second grid electrodes G1 and G2 is uniform. Ions of a given type accelerate into drift chamber 40 at approximately the same time and at the same speed. As a result, thinner bans of ions move into the drift region to achieve enhanced resolution. Additionally, sensitivity is improved because the ions are concentrated in the relatively small space of the potential well 50 defined between the first and second grid electrodes G1 and G2.

While the invention has been described with respect to a preferred embodiment, it is apparent that various changes can be made without departing from the scope of the invention as defined by the appended claims.

What is claimed is:

1. An ion mobility spectrometer, comprising:
   an inlet for receiving a sample to be tested for the presence of at least one substance of interest;
   an ionization chamber having an upstream end communicating with the inlet and a downstream end;
   a drift chamber having an upstream end communicating with the downstream end of the ionization chamber and a downstream end opposed to the upstream end thereof;
   a collector electrode in proximity to the downstream end of the drift chamber for collecting ions passing through the drift chamber;
   first and second grid electrodes lying substantially in first and second planes aligned substantially parallel to one another substantially at an interface between the downstream end of the ionization chamber and the upstream end of the drift chamber so that the second grid electrode is between the first grid electrode and the collector electrode; and
   a controller for applying a slight potential bias to the first grid electrode relative to the second grid electrode and walls of the ionization chamber during accumulation phase for accumulating ions between the first and second grid electrodes, the controller further being operative for applying a pulse to the first grid electrode for accelerating ions accumulated between the first and second grid electrodes into the drift chamber and towards the collector electrode.

2. The ion mobility spectrometer of claim 1, wherein the second grid electrode and the upstream end of the drift chamber are maintained at substantially a common potential when the pulse is applied to the first grid electrode.

3. The ion mobility spectrometer of claim 2, wherein a voltage of approximately 1,000 volts is applied to the second grid electrode when the pulse is applied to the first grid electrode for accelerating ions between the first and second grid electrodes into the drift chamber.

4. The ion mobility spectrometer of claim 1, wherein the ionization chamber includes a substantially cup-shaped chamber wall formed from a conductive material.

5. The ion mobility spectrometer of claim 1, wherein the controller is operative for applying a negative bias to the first grid electrode for a positive ion mode of operation and for applying a positive bias to the first grid electrode for negative ion mode operation.

6. A method for operating an ion mobility spectrometer to determine whether trace amounts of substances of interest are present in a sample, the ion mobility spectrometer having an inlet for receiving a sample to be tested for the trace amounts of the substance of interest, an ionization chamber communicating with the inlet, first and second substantially parallel grid electrode disposed sequentially substantially at a downstream end of the ionization chamber and a drift chamber downstream from the second grid electrode, said method comprising:
   operating the ion mobility spectrometer during an ion accumulation phase by applying a potential bias to the first grid electrode relative to both peripheral walls of the ionization chamber and the second grid electrode for defining a potential well between the first and second grid electrodes that accumulates a narrow band of ions therein;
   applying a pulse to the first grid electrode while maintaining the second grid electrode substantially at a potential defined by the drift chamber for accelerating the narrow band of ions from the potential well defined between the first and second grid electrodes.

7. The method of claim 6, wherein the step of applying a potential bias to the first grid electrode comprises applying a negative bias to the first grid electrode for a positive ion mode of operation to detect narcotics in the sample.

8. The method of claim 6, wherein the step of applying a potential bias to the first grid electrode comprises providing a positive bias to the first grid electrode for operating the ion mobility spectrometer in a negative mode to test samples for the presence of explosives.

9. The method of claim 6, wherein the step of applying a pulse comprises a pulse for a duration of 0.1-0.2 mS.

10. The method of claim 9, further comprising adjusting the second grid electrode to a voltage substantially corresponding to voltage existing in adjacent portions of the drift chamber while the pulse is applied to the first grid electrode.

* * * * *